US00PP25560P3

(12) United States Plant Patent

Klemm et al.

(10) Patent No.: US PP25,560 P3

(45) Date of Patent: May 12, 2015

(54) *LOBELIA* PLANT NAMED 'KLELE13476'

(50) Latin Name: *Lobelia erinus*
Varietal Denomination: KLELE13476

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 168 days.

(21) Appl. No.: 13/986,950

(22) Filed: Jun. 18, 2013

(65) Prior Publication Data

US 2014/0373240 P1 Dec. 18, 2014

(51) Int. Cl.
*A01H 5/00* (2006.01)

(52) U.S. Cl.
USPC ..... Plt./451

(58) Field of Classification Search
USPC ..... Plt./451
See application file for complete search history.

(56) References Cited

PUBLICATIONS

PLUTO Plant Variety Database 20150114 East STN.*

* cited by examiner

*Primary Examiner* — Annette Para

(74) *Attorney, Agent, or Firm* — James M. Weatherly; Bethany R. Roahrig; Cochran Freund & Young LLC

(57) ABSTRACT

A new *Lobelia* plant particularly distinguished by having compact vigor, half-hanging habit and a medium earliness is disclosed.

1 Drawing Sheet

Genus and species: *Lobelia erinus.*
Variety denomination: 'KLELE13476'.

BACKGROUND OF THE NEW PLANT

The present invention comprises a new and distinct variety of *Lobelia,* botanically known as *Lobelia erinus,* and hereinafter referred to by the variety name 'KLELE13476'. 'KLELE13476' originated from an open pollination between the proprietary female *Lobelia* variety 'A 342' (unpatented), having a flat habit with a medium vigor and an unknown male *Lobelia* variety.

In September of 2009 the two *Lobelia* parental lines, 'A 342' and an unknown *Lobelia* were crossed by open pollination in Stuttgart, Germany and seeds were obtained. The seeds were sown and plants were grown for evaluation. A plant line was selected in May 2010 which had compact vigor, a half-hanging habit and a medium earliness and named 'KLELE13476'. In May 2010 'KLELE13476' was first vegetatively propagated by vegetative cuttings. 'KLELE13476' was found to reproduce true to type in successive generations of asexual propagation via cuttings and tissue culture.

CROSS REFERENCE TO RELATED APPLICATIONS

Plant Breeder's Rights for 'KLELE13476' were applied for in Canada on Feb. 8, 2013, Application No. 13-7920. 'KLELE13476' has not been made publicly available or sold more than one year prior to the filing date of this application.

SUMMARY

The following are the most outstanding and distinguishing characteristics of this new variety when grown under normal horticultural practices in Stuttgart, Germany.

1. Compact vigor;
2. Half-hanging habit; and
3. Medium earliness.

DESCRIPTION OF THE PHOTOGRAPH

This new *Lobelia* plant is illustrated by the accompanying photograph which shows a close-up of the flowers. The photograph is of a four-month-old plant grown in a controlled greenhouse environment in Stuttgart, Germany under greenhouse conditions in May 2012. The colors shown are as true as can be reasonably obtained by conventional photographic procedures.

DESCRIPTION OF THE NEW VARIETY

The following detailed descriptions set forth the distinctive characteristics of 'KLELE13476'. The data which define these characteristics were collected from asexual reproductions carried out in Stuttgart, Germany. Data was collected on three-month-old plants grown in a controlled greenhouse environment in Stuttgart, Germany under greenhouse conditions in April of 2013. Color references are to The R.H.S. Colour Chart of The Royal Horticultural Society of London (R.H.S.), $5^{th}$ edition (2007).

Classification:

*Family.*—Campanulaceae.
*Botanical.*—*Lobelia erinus.*
*Common.*—*Lobelia* Designation: 'KLELE13476'.
*Female parent.*—'A 342' (unpatented).
*Male parent.*—Unknown.

Growth:

*Growth and branching habit.*—Compact vigor, half-hanging.

*Form.*—Rounded.

*Height* (*measured from the top of the soil including any flowers*).—10.0 cm.

*Width* (*horizontal plant diameter, including any flowers*).—29.0 cm.

*Time to produce a finished flowering plant.*—8 weeks.

*Outdoor plant performance.*—Very good.

*Time to initiate roots.*—2 weeks.

*Root description.*—Fine, white.

Leaves:

*Arrangement.*—Alternate.

*Color.*—Immature Leaf: Upper surface: RHS 143A. Lower surface: RHS 138C. Mature Leaf: Upper surface: RHS 137B. Lower surface: RHS 138C.

*Length.*—4.0 cm to 5.0 cm.

*Width.*—1.0 cm to 2.0 cm.

*Shape.*—Elliptical to lanceolate, with upper leaves more lanceolate.

*Margin.*—Serrate, with lanceolate leaves partly with entire margins.

*Apex.*—Obtuse.

*Base.*—Acute.

*Texture.*—Upper surface: Hairy (but only very little). Lower surfaces: Smooth.

*Venation.*—Pinnate.

Stems:

*Length.*—10.0 cm to 12.0 cm.

*Diameter.*—0.2 cm.

*Internode length.*—1.5 cm to 2.5 cm.

*Stem color.*—RHS 143A.

*Texture.*—Hairy.

*Stem anthocyanin.*—Absent.

*Peduncle.*—Length: 2.0 cm to 2.5 cm. Diameter: 0.05 cm. Color: RHS 141C. Texture: Smooth.

Flower buds:

*Shape.*—Inverse drop.

*Diameter.*—0.25 cm.

*Length.*—1.0 cm.

*Color.*—RHS 150D.

Inflorescence:

*Blooming habit.*—Continuous.

*Lastingness of individual blooms on plant.*—About 1 week.

*Fragrance.*—Absent.

*Inflorescence type.*—Raceme.

*Quantity of flowers and buds per flowering branch.*—8 to 12.

Flowers:

*Flower diameter* (*horizontal*).—1.8 cm.

*Flower height* (*vertical*).—0.6 cm.

*Mature flower.*—Upper lobe: Color: Upper surface: RHS NN155D. Lower surface: RHS NN155D. Length: 0.7 cm. Width: 0.2 cm. Shape: Lanceolate. Apex: Acute. Margin: Entire. Texture: Upper surface: Smooth. Lower surface: Smooth. Lower lobes: Color: Upper surface: RHS NN155D. Lower surface: RHS NN155D. Length: 1.0 cm. Width: 0.7 cm. Shape: Obovate. Apex: Obtuse. Margin: Entire. Texture: Upper surface: Smooth. Lower surface: Smooth. Corolla tube: Color inside: RHS NN155D. Color outside: RHS NN155D. Tube length: 0.5 cm. Diameter: 0.2 cm. Calyx: Length: 0.2 cm fused part and 0.7 cm non-fused part. Diameter: 0.1 cm. Shape: Funnel, star-shaped (sepals are fused in lower half). Apex: Acute. Texture: Smooth. Color: RHS 137B.

Reproductive organs:

*Stamens.*—Quantity per flower: 5. Filament length: 0.5 cm. Filament color: RHS N155D. Anther length: 0.2 cm. Anther width: 0.1 cm. Anther color: RHS N77C. Pollen amount: Moderate. Pollen color: Greyed Yellow.

*Pistils.*—Quantity per flower: 1. Pistil length: 0.7 cm. Stigma shape: Rounded, two-sided. Stigma color: Mature: RHS N77C. Style length: 0.6 cm. Style color: RHS 142C. Ovary color: RHS 142B.

Fruit and seed set: No fruit or seed set observed, however later in the year fruit and seed set is observed.

Disease and pest/insect resistance: No disease or pest/insect resistance Observed.

COMPARISON WITH PARENTAL LINE AND KNOWN VARIETY

'KLELE13476' is a distinct variety of *Lobelia* having a compact vigor and half-hanging habit; 'KLELE13476' is distinguished from its parents as described in Table 1:

TABLE 1

Comparison with Parental Line

| Trait | Variety 'KLELE13476' | Female parent 'A 342' |
|---|---|---|
| Vigor | Compact | Medium vigor |
| Habit | Half hanging | Flat |

'KLELE13476' is a distinct variety of *Lobelia* having compact vigor and half hanging habit. 'KLELE13476' is most similar to the *Lobelia* plant named 'KLELE11769' (U.S. application Ser. No. 13/506,046), also known as Magadi™ Basket 'White'. Differences between the two varieties are described in Table 2:

TABLE 2

Comparison with Similar Variety

| Trait | Variety 'KLELE13476' | Commercial line 'KLELE11769' |
|---|---|---|
| Vigor | Compact | Medium vigorous |
| Habit | Half hanging | Flat |
| Earliness | Medium early | Later |

We claim:

1. A new and distinct variety of *Lobelia* plant named 'KLELE13476' as shown and described herein.

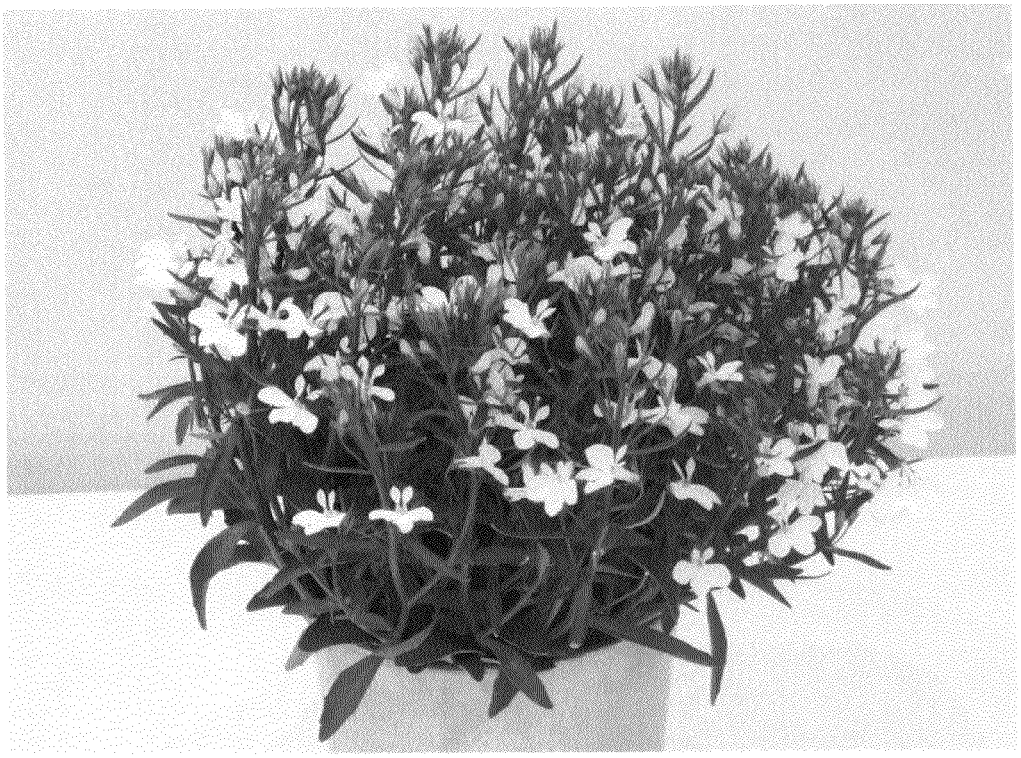

* * * * *